US005658798A

United States Patent [19]
Bertin et al.

[11] Patent Number: 5,658,798
[45] Date of Patent: Aug. 19, 1997

[54] DETECTION OF PROCESS COMPONENTS IN FOOD PROCESS STREAMS BY FLUORESCENCE

[75] Inventors: Gregory K. Bertin, Oak Park; Theresa P. Cawley, Brookfield; John E. Hoots, St. Charles; Brian V. Jenkins, LaGrange Park; Christine M. Stuart, Wheaton; Terry L. Stuebner, Naperville, all of Ill.

[73] Assignee: Nalco Chemical Company, Naperville, Ill.

[21] Appl. No.: 597,415

[22] Filed: Feb. 8, 1996

[51] Int. Cl.$^6$ .................................................. G01N 21/64
[52] U.S. Cl. ........................ 436/3; 436/20; 436/21; 436/22; 436/24; 436/172
[58] Field of Search ................ 250/302; 436/20–24, 436/3, 172, 52, 56; 422/62

[56] References Cited

U.S. PATENT DOCUMENTS

| | | | |
|---|---|---|---|
| 2,827,364 | 3/1958 | Ladisch | 436/20 |
| 4,026,666 | 5/1977 | Holmes | 436/20 |
| 4,253,848 | 3/1981 | Porter | 436/20 |
| 4,783,314 | 11/1988 | Hoots et al. | |
| 4,966,711 | 10/1990 | Hoots et al. | |
| 4,992,380 | 2/1991 | Moriarty et al. | |
| 5,006,311 | 4/1991 | Hoots et al. | |
| 5,041,386 | 8/1991 | Pierce et al. | |
| 5,132,096 | 7/1992 | Hoots et al. | |
| 5,304,800 | 4/1994 | Hoots et al. | |
| 5,320,967 | 6/1994 | Avallone et al. | |
| 5,341,805 | 8/1994 | Stavridi et al. | |
| 5,389,548 | 2/1995 | Hoots et al. | |
| 5,411,889 | 5/1995 | Hoots et al. | |
| 5,416,323 | 5/1995 | Hoots et al. | |
| 5,435,969 | 7/1995 | Hoots et al. | |
| 5,474,910 | 12/1995 | Alfano | 436/20 |

FOREIGN PATENT DOCUMENTS 4234466  4/1994  Germany.

*Primary Examiner*—Jeffrey Snay
*Attorney, Agent, or Firm*—Robert A. Miller; James J. Drake

[57] ABSTRACT

The invention is a method of monitoring for the presence of certain constituents of food processing streams by measurement of fluorescence. The constituent monitored can be a fluorescing impurity of a food product, or the food product itself if such naturally fluoresces. Moreover, losses of the constituent to be monitored may be determined by concurrent measurement of fluorescence of a fluorescent material added to the food process stream. The method is applicable to the following food processing streams among others: meat, vegetable oil, sugar beet, sugar cane, grain, poultry, fruit and soybean processing streams. Upon determination of a variation of the fluorescing constituent to be measured, the food process can be adjusted accordingly.

29 Claims, No Drawings

DETECTION OF PROCESS COMPONENTS IN FOOD PROCESS STREAMS BY FLUORESCENCE

FIELD OF THE INVENTION

The invention is a method of monitoring for the presence of certain constituents of food processing streams by measurement of fluorescence. The constituent monitored can be a fluorescing impurity of a food product, or the food product itself if such naturally fluoresces. Moreover, looses of the constituent to be monitored may be determined by concurrent measurement of fluorescence of a fluorescent material added to the food process stream. The method is applicable to the following food processing streams among others: meat, vegetable oil, sugar beet, sugar cane, grain, poultry, fruit and soybean processing streams. Upon determination of a variation of the fluorescing constituent to be measured, the food process can be adjusted accordingly.

BACKGROUND OF THE INVENTION

The food processing industry employs vast quantities of water to create purified food products. Among the food industries with high volumes of water requirements are the sugar cane, sugar beet processing, fruit and vegetable processing, meat and poultry processing, grain processing, fat and oil processing and dairy product processing industries. Unit operations which are most common to the various types of food processing listed above include boiling and cooling. Boiling or cooling operations have a high demand for make-up water. Much of that water could be re-used in processing operations of it is sufficiently purifies. However, there are strict requirements imposed upon this purification process imposed by the FDA, which limit the choice of chemicals for recycle water treatment.

The first step toward the purification of food processing recyclable waters is the detection of those impurities present in the food processing stream which must be removed. Once that determination has been made, appropriate steps may be taken to purify the water, or to prevent contaminations altogether whenever possible. It must be noted that any method for detection of impurities must also conform to FDA requirements if it involves a chemical additive to the water utilized for the processing of food. Therefore, there is an ongoing need for FDA-acceptable methods of detection of impurities.

The problems associated with the recycling of make-up water for boilers may be taken as exemplary in the evaluation of the need for efficient methods for detection of impurities in the food processing system. Boiler feedwater, which normally is comprised of both makeup water and recirculated condensate water, contains some impurities regardless of the extent to which such waters are treated before being fed to a boiler. When steam is generated, substantially pure water vapor is discharged from the boiler, leaving the impurities (the dissolved and suspended solids) behind, which results in the increase of their concentration in the boiler water. The discharged steam is replaced by contaminant-containing feedwater. An ever increasing concentration of dissolved and suspended solids in the boiler water inevitably results in very serious problems, including deposit formation, corrosion, foaming and carry over, decreased heat transfer efficiency, boiler tube failure or occlusion, for example. Boiler-impurities concentration (boiler solids concentration) is offset by withdrawing water as normal blowdown. The heat energy in the normal blowdown, however, is a major factor reducing a boiler's thermal efficiency, and therefore a blowdown rate in excess of that required to limit solids concentration should be avoided. An excessive blowdown rate also unnecessarily increases water costs.

The use of inert tracer materials to monitor and control the concentration of treatment chemical products (e.g., those containing corrosion and scale inhibitors) in industrial water systems is well-known. Hoots (U.S. Pat. No. 4,783,314) discloses the use of inert tracer materials for monitoring and controlling the concentration of treatment chemical products, corrosion and scale inhibitors, using fluorometry. Hoots et at. (U.S. Pat. Nos. 4,966,711 and 5,041,386) teaches the use of inert fluorescent additives which are added in direct proportion to the amount of a corrosion and/or scale inhibitor to monitor the concentration of a corrosion and/or scale inhibitor in a given industrial water system. U.S. Pat. Nos. 4,992,380; 5,006,311; 5,132,096 and 5,320,967 disclose methods and equipment to monitor fluorescent tracers used in industrial water treatment applications.

Leak detection for temperature-conditioning fluids of the food processing industry among others are disclosed in Hoots et al. U.S. Pat. Nos. 5,304,800 and 5,416,323.

Additionally, Hoots et al. (U.S. Pat. Nos. 5,411,889; 5,389,548 and 5,435,969) do teach monitoring by fluorescence in industrial water systems which may include water systems of the food processing industry. Yet in each of those patents, the material to be monitored is a water treatment agent such as a scale inhibitor, a corrosion inhibitor, a dispersant, a surfactant or an anti-foaming agent. However, none of these three patents directly address the particular problems of the food processing industry as disclosed herein.

Moreover, there is little reference to the use of fluorescence for the monitoring of food processing streams. A disclosure of fluorescence for the monitoring of glucose in food processes is U.S. Pat. No. 5,341,805. German patent DE 4234466 discloses a method for determining the concentration of a tracer-containing active agent in aqueous or non-aqueous active-agent solutions employed particularly in cleaning or disinfecting containers such as bottles, kegs, chests, and tanks and/or pipelines. Essentially, a method is provided wherein it is possible to determine the proper dosage of cleaning solutions utilized to clean food containers such that they are ready for use. That disclosure concerns packaging applications, and not the monitoring of food process streams during food production, as the instant invention. Therefore, there is a demand within the food processing industry for a rapid and efficient method for monitoring food process streams. The present invention fulfills these requirements.

SUMMARY OF THE INVENTION

The invention is a method of monitoring for the presence of certain constituents of food processing streams by measurement of fluorescence. The constituent monitored can be a fluorescing impurity of a food product, or the food product itself if such naturally fluoresces. Moreover, losses of the constituent to be monitored may be determined by concurrent measurement of fluorescence of a fluorescent material added to the food process stream. The method is applicable to the following food processing streams among others: meat, vegetable oil, sugar beet, sugar cane, grain, poultry, fruit and soybean processing streams. Upon determination of a variation of the fluorescing constituent to be measured, the food process can be adjusted accordingly.

DESCRIPTION OF THE INVENTION

The invention is a method for the monitoring of the variation in amount of fluorescing impurities during food processing in food process streams which contain fluorescing impurities comprising the steps of:

A) adding a known amount of a substantially inert fluorescent material to said food process stream;

B) measuring the fluorescence emission wavelengths of the fluorescent impurity and the fluorescent material of step A over time utilizing a fluorometer;

C) calculating the ratio of the fluorescence of the fluorescent impurity to the fluorescence of the fluorescent material of step A;

D) determining from the change in the ratio of step C over time that a variation in the amount of the fluorescing impurity in the food process stream has occurred; and E) adjusting the food process appropriately to compensate for the measured variation in the amount of the fluorescing impurity in said food process streams. The term food as used herein is defined as nutrients for both humans and animals. The fluorescing impurity as used herein is defined as either a component which naturally occurs with the food product of interest, or may also be a component which is a by-product of the food processing.

Useful fluorescent materials for the practice of this invention may be selected from the group consisting of naphthalene sulfonate salt, mono- and dimethyl naphthalene sulfonate salt, 1,5 naphthalene disulfonate salt, 2-naphthalene sulfonate salt, riboflavin, tyrosine, beta carotene, 1-tryptophan, sodium lignosulfonate, sodium humate, fluorescene and 1-dopa. As used herein, the term mono- and dimethyl naphthalene sulfonate salt refers to a proprietary mixture of mono and dimethyl substituted naphthalene sulfonate sodium salts, which are available from Witco Corporation of Houston, Tex. under the trade name of Petro AA Powder. A salient feature of this material is that it is approved by the FDA for certain uses in conjunction with food processing.

The constituent monitored can be a fluorescing impurity of a food product, or the food product itself if such naturally fluoresces. For example amino acids and nitrosamines fluoresce among others.

Monitoring and calculations applicable to the method described above are as disclosed in U.S. Pat. Nos. 4,992,380 and 4,783,314 which are hereinafter incorporated by reference. The term measuring the fluorescence emission wavelengths as used herein is defined as the measurement of wavelengths at specified excitation.

The food processing stream may be selected from the group consisting of meat, vegetable oil, sugar beet, sugar cane, grain, poultry, fruit and soybean processing streams. As used herein, the term grain processing encompasses brewing as well as solid food production. In one aspect of the invention, the food processing stream is a sugar beet processing stream and the fluorescent material is mono- and dimethyl naphthalene sulfonate salt. The food process may be selected from the group consisting of boiling, chilling, drying, purifying, crystallizing, extracting, pasteurizing, thermal processing, grinding, pH adjustment, softening, waste treatment and clarifying.

The concentration of the fluorescent material added to the food process stream is from about 0.1 ppb to about 250 ppm. Preferably, the concentration of the fluorescent material added to the food process stream is from about 0.5 ppb to about 100 ppm. Most preferably, the concentration of the fluorescent material added to the food process stream is from about 1 ppb to about 25 ppm. However, the amount may vary according to the type of process stream monitored, because there may be differing levels of background fluorescence depending upon the particular food. The measurement of the fluorescence may be continuously monitored by a fluorometer.

Another aspect of the invention is a method for the determination of the presence of contaminating food process streams which contain fluorescent moieties in the circulating water of food processing equipment which contains circulating water comprising the steps of:

A) adding a known amount of a substantially inert fluorescent material to said circulating waters;

B) measuring the fluorescence emission wavelengths of the fluorescent moiety and the fluorescent material of step A over time utilizing a fluorometer;

C) calculating the ratio of the fluorescence of the fluorescent moiety to the fluorescence of the fluorescent material of step A;

D) determining from the change in the ratio of step C over time that a contamination of the circulating water of the food processing equipment has occurred; and E) adjusting the food process appropriately to avoid further contamination of said food processing equipment.

Methods for the calculation of the ratios of fluorescence and their relationship to the detection of leaks are disclosed in U.S. Pat. Nos. 5,304,800 and 5,416,323 which are hereinafter incorporated by reference. As above, the useful fluorescent materials for the practice of this invention may be selected from the group consisting of naphthalene sulfonate salt, mono- and dimethyl naphthalene sulfonate salt, 1,5 naphthalene disulfonate salt, 2-naphthalene sulfonate salt, riboflavin, tyrosine, beta carotene, 1-tryptophan, sodium lignosulfonate, sodium humate, fluorescene and 1-dopa.

The constituent monitored can be a fluorescing impurity of a food product, or the food product itself if such naturally fluoresces. For example amino acids and nitrosamines fluoresce among others.

The food processing stream may be selected from the group consisting of meat, vegetable oil, sugar beet, sugar cane, grain, poultry, fruit and soybean processing streams. The food processing stream may be a sugar beet processing stream and the fluorescent material may be mono- and dimethyl naphthalene sulfonate salt. The food processing equipment which contains circulating water may be selected from the group consisting of boilers, chillers, evaporators, pasteurizers, and thermal processors.

The concentration of the fluorescent material added to the food process stream is from about 0.1 ppb to about 250 ppm. Preferably, the concentration of the fluorescent material added to the food process stream is from about 0.5 ppb to about 100 ppm. Most preferably, the concentration of the fluorescent material added to the food process stream is from about 1 ppb to about 25 ppm.

The measurement of the fluorescence may be continuously monitored by a fluorometer.

A further aspect of the invention is a method for quantifying the mount of a food substance present in a food processing stream wherein the food substance is present in a known ratio to a fluorescing moiety in the food processing stream comprising the steps of:

A) adding a known amount of a substantially inert fluorescent material to said food process stream;

B) measuring the fluorescence emission wavelengths of the fluorescing moiety and the fluorescent material of step A over time utilizing a fluorometer;

C) calculating the ratio of the fluorescence of the fluorescent moiety to the fluorescence of the fluorescent material of step A; and D) determining from the change in the ratio of step C over time that a proportional variation in the amount of the food substance in the food processing stream has occurred.

Useful fluorescent materials for the practice of this invention may be selected from the group consisting of naphthalene sulfonate salt, mono- and dimethyl naphthalene sulfonate salt, 1,5 naphthalene disulfonate salt, 2-naphthalene sulfonate salt, riboflavin, tyrosine, beta carotene, 1-tryptophan, sodium lignosulfonate, sodium humate, fluorescene and 1-dopa.

The constituent monitored can be a fluorescing impurity of a food product, or the food product itself if such naturally fluoresces. For example, amino acids and nitrosamines fluoresce among others.

The food processing stream may be selected from the group consisting of meat, vegetable oil, sugar beet, sugar cane, grain, poultry, fruit and soybean processing streams. The food substance may be selected from meat, poultry, beet sugar, sugar cane, grain, soybeans, fruit and vegetable oil. The food processing stream may be a sugar beet processing stream and the fluorescent material may be mono- and dimethyl naphthalene sulfonate salt.

For the practice of this invention, the fluorescing moiety may be selected from the group consisting of: DC Red 22, DC Green 8, FDC Red 2, DC Yellow 10, DC Green 5, FDC Blue 1, FDC Blue 2, FDC Yellow 5 and FDC Yellow 6.

DC Green 5 as used herein refers to Benzenesulfonic acid, 2,2'-[(9,10-dihydro-9,10-dioxo-1,4-anthracenediyl)diimino bis[5-methyl], disodium salt. DC Green 8 as used herein refers to Pyrene, 4-hydroxy-1,6,9-trisulfonic acid, trisodium salt. DC Red 22 as used herein refers to Spiro [isobenzofuran-1(3H), 9'-[9H]xanthen]-3-one, 2',4',5',7'-tetrabromo-3',6'-dihydroxy-, disodium salt. DC Yellow 10 as used herein refers to sodium salts of: 2-(2,3-dihydro-1,3-dioxo-1H-indene-2-yl)-6-quinoline sulfonic acid and 2-(2,3-dihydro-1,3-dioxo-1-H-indene-2-yl)-8-quinoline sulfonic acid. FDC Blue 1 as used herein refers to Benzenemethanaminium, N-ethyl-N-[4-[[4-[ethyl[(3-sulfophenyl)methyl]amino]phenyl](2-sulfophenyl)methylene]-2,5-cyclohexadien-1-ylidene]-3-sulfo-, hydroxide, inner salt, disodium salt. FDC Blue 2 as used herein refers to 1H-Indole-5-sulfonic acid, 2-(1,3-dihydro-3-oxo-5-sulfo-2H-indol-2-ylidene]-2,3-dihydro-3-oxo-, disodium salt. FDC Red 2 as used herein refers to 2,7-Naphthalenedisulfonic acid, 3-hydroxy-4-[(4-sulfo-1-naphthalenyl)aza]-, trisodium salt. FDC Yellow 5 as used herein refers to 1H-Pyrazole-3-carboxylic acid, 4,5-dihydro-5-oxo-1-(4-sulfophenyl)-4-[(4-sulfophenyl)azo]-, trisodium salt. FDC Yellow 6 as used herein refers to 4-(2-hydroxy-6-sulfonyl-1-naphthylazo)benzenesulfonic acid, disodium salt.

The concentration of the fluorescent material added to the food process stream is from about 0.1 ppb to about 250 ppm. Preferably, the concentration of the fluorescent material added to the food process stream is from about 0.5 ppb to about 100 ppm. Most preferably, the concentration of the fluorescent material added to the food process stream is from about 1 ppb to about 25 ppm.

The measurement of the fluorescence may be continuously monitored by a fluorometer. Furthermore, the food process may be adjusted appropriately to compensate for the variation in the amount of the food substance in said food processing stream.

The invention is also a method for the monitoring of the variation in amount of fluorescing impurities present in food process streams during food processing comprising the steps of:

A. measuring the fluorescence emission wavelengths of the fluorescing impurity of the food processing stream over time utilizing a fluorometer; and B. adjusting the food process appropriately to compensate for the measured variation in the amount of the fluorescing impurity in said food processing streams over time.

The constituent monitored can be a fluorescing impurity of a food product, or the food product itself if such naturally fluoresces. For example amino acids and nitrosamines fluoresce among others.

The food process stream may be selected from the group consisting of meat, vegetable oil, sugar beet, sugar cane, grain, poultry, fruit and soybean processing streams. The food process may be selected from the group consisting of boiling, chilling, drying, purifying, crystallizing, extracting, pasteurizing, thermal processing, grinding, pH adjustment, softening, waste treatment, and clarifying. The measurement of the fluorescence may be continuously monitored by a fluorometer.

The invention is also a method for the determination of the presence of contaminating food process streams which contain fluorescent moieties in circulating water of the food processing equipment which contains circulating water comprising the steps of:

A. monitoring for the fluorescence emission wavelengths of said fluorescent moieties in said circulating water over time utilizing a fluorometer; and B. adjusting the food process appropriately to avoid further contamination in said food processing equipment when said fluorescence emission wavelength is observed.

The constituent monitored can be a fluorescing impurity of a food product, or the food product itself if such naturally fluoresces. For example amino acids and nitrosamines fluoresce among others.

The food processing stream may be selected from the group consisting of meat, vegetable oil, sugar beet, sugar cane, grain, poultry, fruit and soybean processing streams. The food processing equipment may be selected from the group consisting of boilers, chillers, evaporators, pasteurizers and thermal processors. The measurement of the fluorescence may be continuously monitored by a fluorometer.

A further aspect of the invention is a method for quantifying the amount of a food substance present in a food processing stream wherein the food processing stream contains a food substance and a fluorescing moiety in a known ratio comprising the steps of:

A. measuring the fluorescence emission wavelengths of the fluorescing moiety over time utilizing a fluorometer; and B. determining from the change in the amount of fluorescence that a proportional variation in the amount of the food substance in the food processing stream has occurred.

The constituent monitored can be a fluorescing impurity of a food product, or the food product itself if such naturally fluoresces. For example amino acids and nitrosamines fluoresce among others.

The food processing stream may be selected from the group consisting of meat, vegetable oil, sugar beet, sugar cane, grain, poultry, fruit and soybean processing streams. The food substance may be selected from the group consisting of meat, poultry, beet sugar, sugar cane, grain, soybeans, fruit and vegetable oil. The fluorescing moiety may be selected from the group consisting of: FDC Red 22, FDC Green 8, FDC Red 2, FDC Yellow 10, FDC Green 5, FDC Blue 1, FDC Blue 2, FDC Yellow 5 and FDC Yellow 6. The measurement of the fluorescence may be continuously monitored by a fluorometer. Thereafter, the food process may be adjusted appropriately to compensate for the variation in the amount of the food substance in said food processing stream.

Conditions for the use of tracer materials for leak detection within the boiler of a food processing system may serve to illustrate some general aspects of the invention. Generally it is desirable to employ the least amount of inert tracer that is practical for the circumstance, and the amount of the inert tracer added to the water of the boiler system should be at least an amount effective for the determinations desired. Seldom would an inert tracer be deliberately fed to the water of a boiler system in an amount grossly in excess of the minimum effective amount because there generally would be no practical purpose in doing so that would justify the costs involved and any deleterious effects on the quality of the water of the boiler caused by the presence of the inert tracer therein. The amount of inert tracer to be added to the water of the boiler system that is effective without being grossly excessive will vary with a variety of factors including, without limitation, the inert tracer and monitoring method selected, the potential for background interference with the selected monitoring method, the magnitude of the expected inert tracer concentration in the blowdown, the monitoring mode (which generally would be an on-line continuous monitoring mode), and other similar factors. Generally the dosage of an inert tracer to a water of the boiler system will be at least sufficient to provide a concentration of tracer in the blowdown at steady state of at least about 0.1 ppb, and more commonly at least about 5 ppb or higher, up to about 100 or 250 ppm, in the blowdown.

By the terms "tracing" is meant herein, unless expressly indicated otherwise, the determination of the concentration of the inert tracer(s) in the blowdown Such tracing would seldom be conducted on a singular intermittent or semi-continuous basis for the purpose of the present invention, but instead on a substantially continuous basis, and preferably the concentration determination is conducted on-site (at the site of the boiler system) to provide a rapid detection of the fact that the inert tracer concentration in the boiler or blowdown has dropped from the normal concentration or that the blowdown flow rate has decreased compared to normal. The inert tracer is at times referred to herein merely as a "tracer".

As noted above, the inert tracer must be added to the water of the boiler system in known proportion to the feedwater, and preferably the inert tracer is introduced into the boiler system together with the feedwater at a known and constant concentration therein. The tracer formulation, or "product", may be an aqueous solution or other substantially homogeneous admixture that disperses with reasonable rapidity in the system to which it is added. Since in most any instance an inert tracer would be added to a boiler system as a component of a formulation, rather than as dry solid or neat liquid, the tracer concentration may be correlated not to the numerical concentration of the inert tracer itself, but instead to the concentration of a product, which in turn can be correlated to the concentration of the inert tracer when and if such information is required.

A chemical compound(s) selected as an inert tracer(s) should not be one that is consumed or lost to the water of the boiler system, for instance due to degradation, deposition, complexation, or other phenomena, unless such consumption or loss is at a rate that is predictable. The inert tracer(s) used in the present invention is preferably substantially unconsumed in the use environment. An inert tracer(s) that is wholly inert in the water-system environment would not react with any of the components in the water of the boiler system to which it is added, would not degrade in the environment of the water of the boiler system, would be incapable of coupling and/or depositing in any manner within such boiler system and would not appreciably be effected by other system parameters such as metallurgical composition, heat changes or heat content. There are water-soluble inert tracer(s) that are wholly inert, or substantially inert, in the aqueous environments likely to be encountered in industrial boiler systems. Further, an inert tracer has a degree of inertness such that no more than 10 weight percent thereof is lost due to reaction degradation, coupling and/or deposition during the time that elapses between its addition and its discharge as a blowdown component is sufficiently or substantially inert for the purpose of the present invention for most tracer monitorings.

Among these substantially boiler-system-inert fluorescent compounds are the mono-, di-and trisulfonated naphthalenes, including their water-soluble salts, particularly the various naphthalene mono- and disulfonic acid isomers, which are a preferred inert tracer(s) for use in the present invention. The naphthalene mono- and disulfonic acid isomers are water-soluble, generally available commercially and easily detectable and quantifiable by known fluorescence analysis techniques. Many of these inert tracer (s) (mono-, di- and trisulfonated naphthalenes and mixtures thereof) are extremely compatible with the environments of most boiler systems. Among these preferred fluorescent tracers, 2-NSA and (1,5-NDSA) have been found to be thermally stable (substantially inert) at temperatures up to at least about 540° C. (1004° F.), for at least 24 hours at 285° C. (545° F.) and at pressures up to about 1,500 psig for time periods commensurate with commercial boiler holding times. Such inert fluorescent tracers have been found to carryover into the steam discharged from commercial boilers at concentrations of less than 500 ppt (parts per trillion) when present in the boiler waters at concentrations within the range of from about 5 to 50 ppb, and thus these tracers are not selectively carried over into the steam, and do not carry over into the steam in any appreciable amount. In addition, it has been found that the contribution to conductivity of the mono-, di- and trisulfonate naphthalenes is minimal at the ppb levels used for fluorescence determination in either the boiler feedwater or the blowdown.

Another group of inert fluorescent tracers that are preferred for use in the process of the present invention, particularly under pressures of no more than about 1,000 psi, are the various sulfonated derivatives of pyrene, such as 1,3,6,8-pyrene tetrasulfonic acid, and the various water-soluble salts of such sulfonated pyrene derivatives.

In addition to the above, the fluorescent compounds should be soluble or evenly dispersible in the fluid systems to which they are added at the concentration levels employed. Moreover, if intended for use in dilute aqueous systems, the fluorescent compounds should be substantially water-soluble at the concentration levels employed.

Examples of fluorescent compounds which may be employed in this invention include the following: mono-, di-and trisulfonated naphthalenes, including their water soluble salts, particularly the various naphthalene mono-and disulfonic acid isomers, which are preferred inert tracers for use in the present invention. The naphthalene mono- and disulfonic acid isomers are water-soluble, generally available commercially and are easily detectable and quantifiable by known fluorescence analysis techniques. Preferred naphthalene mono- and disulfonic acid isomers are the water-soluble salts of naphthalene sulfonic acid ("NSA"), such as 1-NSA and 2-NSA, and naphthalene disulfonic acid ("NDSA" or "NDA"), for instance 1,2-NDSA, 1,3-NDSA, 1,4-NDSA, 1,5-NDSA, 1,6-NDSA, 1,7-NDSA, 1,8-NDSA, 2,3-NDSA, and 2,4-NDSA. Many of these inert tracer(s) (mono-, di-, and trisulfonated naphthalene and mixtures thereof) are generally compatible with the environments of most aqueous systems for food processing.

Many other water soluble tracer materials that fluoresce will be apparent to those skilled in the art. As a genera/rule, and in the selection of tracers for this invention, tracers should be:

1. substantially inert to the ingredients into which they are to be added;
2. substantially inert to the system into which they are to be added;
3. fluoresce at a wave length that is distinguishable from the wave length of other compounds that may be added to the system;
4. be soluble, or uniformly suspended in the process stream;
5. thermally stable and not decompose at the temperature within the given system to which they are fed;
6. detectable on a continuous or semicontinuous basis and susceptible to concentration measurements that are accurate, repeatable, and capable of being performed on the system to which they are fed;
7. substantially foreign to the chemical species that are normally present in the water to which they are fed;
8. substantially impervious to any of its own potential specific losses from the water of the system to which they are fed;
9. substantially impervious to interference from, or biasing by, the chemical species that are normally present in the water to which they are added;
10. compatible with all treatment agents employed in the system in which the inert tracer may be used, and thus in no way reduce the efficacy thereof;
11. compatible with all mechanical components of the system to which they are to be added; and,
12. reasonably nontoxic and environmentally safe, not only within the system to which they are added, but also upon discharge therefrom.

Generally, it is desirable to employ the least amount of tracer chemical that is practical for the circumstance, and the amount of the tracer added to the fluid should be at least an amount effective for the analysis desired. Seldom would a tracer be deliberately fed to a fluid in an amount grossly in excess of the minimum effective amount because there generally would be no practical purpose in doing so that would justify the costs involved and any deleterious effects on the quality of either of the fluids caused by the presence of the tracer chemical therein.

The tracer is preferably selected from among those that are easily quantifiable by a fluorescence analysis method, a preferred analytical technique for the purposes of the present process. Other analysis methods not excluded for use in quantifying the inert tracer are HPLC and fluorescence analysis combinations, which are described in more detail below.

Fluorescence Emission Spectroscopy

The detection and quantification of specific substances by fluorescence emission spectroscopy is founded upon the proportionality between the mount of emitted light and the amount of a fluoresced substance present. When energy in the form of light, including ultraviolet and visible light, is directed into a sample cell, fluorescent substances therein will absorb the energy and then emit that energy as light having a longer wavelength than the absorbed light. A fluorescing molecule absorbs a photon resulting in the promotion of an electron from the ground energy state to an excited state. When the electron's excited state relaxes from a higher energy vibrationally-excited state, energy is lost in the form of heat. When the electron relaxes to the ground electronic state, light is emitted at a lower energy than that absorbed due to the heat-energy loss, and hence at a longer wavelength than the absorption. The amount of emitted light is determined by a photodetector. In practice, the light is directed into the sample cell through an optical light filter so that the light transmitted is of a known wavelength, which is referred to as the excitation wavelength and generally reported in nanometers ("nm"). The emitted light is similarly screened through a filter so that the amount of emitted light is measured at a known wavelength or a spectrum of wavelengths, which is referred to as the emission wavelength and generally also reported in nanometers. When the measurement of specific substances or categories of substances at low concentrations is desired or required, such as often is the case for the process of the present invention, the filters are set for a specific combination of excitation and emission wavelengths, selected for substantially optimum low-level measurements.

In general, the concentration of an inert tracer can be determined from a comparison of a sample's emissions intensity to a calibration curve of the given tracer's concentration versus emissions, for the same set of excitation wavelength/emission wavelengths. Such a concentration-by-comparison method by which the sensed emissions are converted to a concentration equivalent preferably is employed to determine concentration of an inert tracer that are within the concentration range over which a linear emission response is observed, and this concentration range is referred to herein as the "linear-emission-response concentration range". The linear-emission-response concentration range is to some extent dependent upon the specific inert tracer and the excitation wavelength/emission wavelength set employed. At inert tracer concentrations higher than a given inert tracer's linear-emission-response concentration range, there is a negative deviation from ideal (linear) behavior, the degree of emission for a given concentration being less than predicted by a linear extrapolation. In such instances, the sample can be diluted by known factors until the concentration of the inert tracer therein falls within the linear-emission-response concentration range. If the inert tracer is present in the sample at only very low concentrations, there are techniques for concentrating the inert tracer by known factors until its concentration falls within the linear-emission-response concentration range or is otherwise more readily measured, for instance by liquid-liquid extraction. Nonetheless, preferably a calibration curve over the linear-emission-response concentration range would be prepared or obtained before employing a given inert tracer, and preferably the inert tracer would be added to the feedwater of the boiler system in an amount sufficient to provide a concentration of the inert tracer in the boiler that is within the linear-emission-response concentration range. Generally the linear-emission-response concentration range of an inert tracer is sufficiently broad to readily estimate the amount of the inert tracer that will be sufficient for this purpose. A linear-emission-response concentration range will most often extend through a concentration range from a concentration of "m" to a concentration of at least 10 m.

A determination of the presence of a fluorescent inert tracer and preferably the concentration thereof in the blowdown from a boiler system can be made when the concentration of the inert tracer in the boiler is only several parts per million (ppm) or even parts per billion (ppb) for some of the inert tracer that can be employed in the process of the present invention. In preferred embodiment, the amount of a fluorescent inert tracer added to the boiler system should be sufficient to provide a concentration of the inert tracer in the blowdown to be analyzed of from about 5 ppb to about 100 or 200 ppm, although the preferred inert tracers specifically mentioned herein need not be present in the sample analyzed in excess of about 5 or 7 ppm. Such analyses, that is, the measurements of the light emitted in response to the light transmitted to the blowdown, can be made on-site, preferably on an almost instant and continuous basis, with simple portable equipment, such as the photodetector and screens described above.

At times it may be desired to employ a plurality of inert tracers. For instance, it may be desired to use a plurality of inert tracers to confirm that neither is undergoing any tracer-specific loss or one tracer to detect a given variance and another for the detection of a different variance or other parameter. Such separate and distinct inert tracers can each be detected and quantified in a single water blowdown fraction despite both being fluorescent tracers if their respective wavelengths of emission do not interfere with one another. Thus concurrent analyses for multiple inert tracers is possible by selection of inert tracers having appropriate spectral characteristics. Preferably widely separated wavelengths of radiation should be used to excite each of the inert tracers and their fluorescent emissions should be observed and measured at widely separated emission wavelengths. A separate concentration calibration curve may be prepared or obtained for each inert tracer. In other words, more than one inert tracer can be employed, and then the presence and/or concentration of each such inert tracer in the boiler system should be determined using analytical parameters (particularly the excitation/emission wavelengths) effective for each such inert tracer, which analytical parameters preferably are sufficiently distinct to differentiate between measurements.

Fluorescence emission spectroscopy on a substantially continuous basis, at least over a given time period, is one of the preferred analytical techniques for the process of the present invention. It is one of the preferred analysis techniques for quantifying and determining the concentration of the inert tracer in a boiler system and it is an analysis technique having significant advantages. Fluorescent chemical tracers and monitoring techniques are now known, for instance as disclosed in U.S. Pat. No. 4,783,314, J. E. Hoots and B. E. Hunt, issued November 8, 1988, incorporated herein by reference, wherein inert fluorescent tracers are employed in combination with a fluorescence monitoring, such as the sodium salt of 2-naphthalene sulfonic acid.

When the inert tracer is 2-NSA, one of the water-soluble salts of napththalene sulfonic acid ("NSA"), its concentration in the blowdown from a boiler system can be fluorometrically measured by excitation at 277 nm and emission measurement at 334 nm, and the emissions observed referenced to a standard aqueous solution containing 0.5 ppm 2-NSA, acid actives.

Fluorometers for this purpose are commercially available from a variety of sources. For example, a Gilford Fluoro IV dual-monochromator spectrofluorometer can be used for a fluorometric analysis conducted on an intermittent basis and for on-line fluorescence monitoring, a portable fluorometer equipped with appropriate excitation and emission filters and a quartz flow through cell can be used, such as is commercially available from Turner Designs (Sunnyvale, Calif.) Model Fluorometer 10 AU, which is mentioned above. Preferred fluorometers are available from Nalco Chemical Company, Naperville, Ill. under the trade name TRASAR®.

In general for most fluorescence emission spectroscopy methods having a reasonable degree of practicality, it is preferable to perform the analysis without isolating in any manner the inert tracer. Thus there may be some degree of background fluorescence in the blowdown on which the fluorescence analysis is conducted, which background fluorescence may come from chemical compounds in the boiler system that are unrelated to the present process. In instances where the background fluorescence is low, the relative intensities (measured against a standard fluorescent compound at a standard concentration and assigned a relative intensity for instance 100) of the fluorescence of the tracer versus the background can be very high, for instance a ratio of 100/10 or 500/10 when certain combinations of excitation and emission wavelengths are employed even at flow fluorescent compound concentrations, and such ratios would be representative of a "relative fluorescent" (under like conditions) of respectively 10 and 50. In preferred embodiment, the excitation/emission wavelengths and/or the mount of tracer employed are selected to provide a relative fluorescence anticipated.

For instance, for most boiler water backgrounds, a compound that has a relative fluorescence of at least about 5 at a reasonable concentration is very suitable as an inert tracer. When there is or maybe a specific chemical specie of reasonably high fluorescence in the background, the tracer and/or the excitation and/or emission wavelengths often can be selected to nullify or at least minimize any interference of the tracer measurement(s) caused by the presence of such specie.

One method for the continuous on-stream monitoring of chemical tracers such as the inert tracer by fluorescence emission spectroscopy and other analysis methods is described in U.S. Pat. No. 4,992,380, B. E. Moriarity, J. J. Hickey, W. H. Hoy, J. E. Hoots and D. A. Johnson, issued Feb. 12, 1991, incorporated hereinto by reference.

Combined HPLC-Fluorescence Analysis

The combination of high-pressure liquid chromatography ("HPLC") and fluorescence analyses of fluorescent tracers is a powerful tool for the present process, particularly when very low levels of the inert tracer are used or the background fluorescent encountered would otherwise interfere with the efficacy of the fluorescence analysis. The HPLC-fluorescence analysis method allows the tracer compound to be separated from the fluid matrix and then the tracer concentration can be measured. The combination of HPLC-fluorescence analysis is particularly effective for measuring minute levels of tracer in highly contaminated fluids.

The HPLC method can also be effectively employed to separate a tracer compound from a fluid matrix for the purposes of then employing a tracer-detection method other than the fluorescence analysis, and such other tracer-detection methods include without limitation light absorbance, post-column derivatization, and conductivity among others.

Analytical techniques for quantifying the presence and/or concentration of a chemical species without isolation thereof are within an evolving technology, and the above survey of reasonable analytical techniques for use in monitoring the inert tracer in the process of the present invention may presently not even be exhaustive, and most likely techniques equivalent to the above for the purposes of the present invention will be developed in the future.

An inert tracer may be selected for a given process based on a preference for one or more analytical techniques, or an analytical technique may be selected for a given process based on a preference for one or more inert tracers.

By properly choosing the fluorescent reagent additive to the microbiocides of this invention, quantitative and in-situ measurement of tracer levels from parts per trillion to parts per million can be routinely accomplished on an instant or continuous basis with inexpensive portable equipment.

The application of this invention to the sugar beet processing industry serves as an example of the general utility of this invention for the food processing industry. There are six stages in the processing of sugar beets to extract sugar. They are diffusion, juice purification, evaporation, crystallization, dried-pulp manufacture and recovery of sugar from molasses. This process involves the utilization of large quantities of water and requires boiling of the process stream during several of the steps listed above.

In particular, problems with process stream contamination during the evaporation stage are prevalent. The evaporators, as part of the food processing equipment, utilize boilers which contain circulating water. To increase re-use of water, make-up water for the boiler may be drawn from the evaporator's condensate stream. Occasionally, thin juice which is part of the sugar beet processing stream will carry over into the evaporator condensate stream and ultimately reach the boiler. Within the boiler, organic acids are formed from the breakdown of the contaminating thin juice under high temperature conditions. These acids decrease the pH within the boiler rapidly from a normal condition of approximately pH=10 to approximately pH=4. This rapid gradient pH change can result in significant damage to the boiler. Therefore early and rapid detection of thin juice at low concentrations is desirable to prevent such damage to the food processing equipment.

In the practice of this invention, the natural fluorescence of the components of the thin juice can be utilized to determine the presence of contamination. Among the fluorescing components identified in thin juice are: amino acids such as tryptophan and tyrosine, lipids and phenolic compounds such as 1-dopa. Any of these fluorescent compounds which are native to the sugar beet processing stream may be monitored to determine contamination within the circulating waters of food processing equipment.

Current methods in use for the detection of thin juice carry over into the equipment include sodium analysis and alpha-naphthol testing. However, these tests are inefficient as the sodium analyzer will produce many false positive readings, indicating thin juice contamination when other sodium-containing compounds are detected which are not components of the thin juice sugar beet processing stream. Water treatment chemicals may be responsible for some of the false positive readings. Therefore, there exists a need for a rapid, reliable, on line method for the detection of food process stream contaminations.

The following examples are presented to describe preferred embodiments and utilities of the invention and are not meant to limit the invention unless otherwise stated in the claims appended hereto.

EXAMPLE 1

Fluorescent materials were tested over a range of pH's, at a particular concentration where significant fluorescence was found. The pH range represents typical boiler conditions (8.5–11) and an additional data point at pH=5 was taken to appraise fluorescence of chemistries in an environment exposed to acid upset. The excitation and emission wavelengths are enclosed in parentheses beneath the corresponding fluorescence value at each pH. These values are followed by two sets of coefficients of variation (cov) which is standard deviation/mean×100. Cov 1 represents the typical boiler parameter values (pH=8.5, 10, 11) and Cov 2 represents all four pH conditions. A coefficient of variation less than or equal to 5 indicates no significant deviation of fluorescence with pH. The results of Table I indicate that the fluorescent materials tested are stable over a wide range of pH conditions.

TABLE I

| Tracer | pH | | | | Cov | |
| --- | --- | --- | --- | --- | --- | --- |
| | 5 | 8.5 | 10 | 11 | 1 | 2 |
| FDC Green 8 (100 ppb) | 388.2 (280, 510) | 380.0 (280, 510) | 383.9 (300, 510) | 370.8 (300, 510) | 1.8 | 1.9 |
| | 428.3 (400, 510) | 410.4 (400, 510) | 623.2 (460, 510) | 627.0 (460, 510) | 22.4 | 22.8 |
| FDC Red 22 (100 ppb) | 548.1 (520, 530) | 568.7 (520, 530) | 557.5 (520, 530) | 562.1 (520, 520) | 1.0 | 1.5 |
| | 167.4 (260, 520) | 168.8 (260, 520) | 204.0 (260, 520) | 191.0 (260, 520) | 9.5 | 9.7 |
| FDC Red 2 (10 ppm) | 34.64 (320, 420) | 36.99 (320, 410) | 37.23 (320, 420) | 35.62 (320, 420) | 2.4 | 3.4 |
| A* | 496.2 (280, 340) | 493.0 (280, 340) | 511.1 (285, 340) | 504.5 (280, 340) | 1.8 | 1.6 |
| Riboflavin (1 ppm) | 1187 (260, 520) | 862.4 (260, 510) | 958.5 (260, 510) | 354.1 (260, 510) | 44.8 | 41.8 |
| | 382.8 (380, 520) | 240.2 (360, 520) | 190.5 (360, 510) | 53.11 (360, 510) | 60.1 | 62.8 |
| | 532.5 (440, 520) | 291.2 (440, 520) | 254.6 (440, 520) | 69.38 (440, 510) | 58.0 | 66.3 |
| Sodium humate | 72.07 (460, 520) | 121.9 (460, 520) | 128.2 (480, 530) | 114.2 (480, 530) | 5.8 | 66.3 |

TABLE I-continued

| | pH | | | | Cov | |
|---|---|---|---|---|---|---|
| Tracer | 5 | 8.5 | 10 | 11 | 1 | 2 |
| (100 ppm) | 72.85 (340, 390) | 100.6 (340, 510) | 96.67 (340, 510) | 74.88 (360, 510) | 15.3 | 16.7 |
| Sodium ligno-sulfonate (250 ppm) | 454.9 (320, 390) | 386.2 (320, 400) | 315.0 (320, 420) | 277.6 (340, 440) | 16.9 | 21.9 |
| L-tryptophan (100 ppm) | 55.79 (280, 350) | 59.60 (280, 360) | 143.4 (280, 360) | 151.3 (280, 360) | 43.0 | 50.6 |

A* = mono- and dimethyl naphthalene sulfonate salt (500 ppb)

EXAMPLE 2

To simulate field conditions, thin juice from a sugar beet processing stream which has a pH of 7.9 was added to DI water which had been adjusted to pH 10 to produce the solution concentrations listed below. The final pH's of the solutions tested are indicated.

TABLE II

| | Peak 1 | | Peak 2 | | |
|---|---|---|---|---|---|
| Conc. | EX/EM | Fluor | EX/EM | Fluor | pH |
| 100%* | 400, 480 | 447.1 | — | — | 7.9 |
| 10%* | 340, 420 | 352.7 | 280, 360 | 284.6 | 9.0 |
| 1% | 320, 410 | 67.95 | 280, 360 | 181.9 | 10.0 |
| 0.1% | — | — | 280, 360 | 22.93 | 10.0 |
| 0.01% | — | — | 280, 360 | 3.994 | 10.0 |
| 0.001% | — | — | — | — | 10.0 |

*These solutions were increasingly turbid and colored.

The results indicate that fluorescent moieties within the thin juice can be measured in the range from 10% to 0.01% concentration of thin juice. Thus, the natural fluorescence within the thin juice of the sugar beet processing stream could be utilized to detected contaminations down to low levels.

EXAMPLE 3

Use of Naturally Occurring Fluorescent Compounds for Leak Detection

Many food processing streams contain constituents which fluoresce. Contamination by a process stream through barrier breakage and/or carryover can upset critical support operations such as heat transfer equipment (includes: cooling towers, heat exchangers, thermal processing systems, chillers, boilers, etc.). The natural fluorescence of the process stream can be used to detect a process leak into a nonprocess or fluorescent free stream. Fluorescence detection can be used to detect the presence of a process leak or to divert the process stream from a critical process. For example, many food processes produce large volumes of high quality water suitable for boiler water make-up. Should the make-up stream become contaminated with a food process stream, the water quality no longer would meets make-up water standards. Contaminated make-up water can severely damage a boiler system. The boiler make-up water stream could be monitored at the optimum fluorescence wavelength of the process Stream to detect for the presence of a process leak. Should a leak be detected, the make-up steam could be diverted away from the boiler and an alternative, fresh water source used for make-up. Although this example describes process condensate used for boiler water make-up, similar analogies could be drawn from other systems which might become contaminated with a process stream. One of the detriments of food process stream contamination in food processing equipment which utilizes circulating water (such as a boiler or cooler) is that the food may serve as a nutrient for microorganisms. This additional food source for microorganisms can result in uncontrolled growth which leads to increased fouling within the food processing equipment. Ultimately, equipment so fouled causes a decrease in the efficiency of the food processing system. Diagnosis of the problem in the fashion described above can alleviate the problems associated with food process stream leakages.

EXAMPLE 4

Samples of food processing streams were collected and analyzed for fluorescence. Each sample was scanned over a range of excitation and emission frequencies to quantify fluorescence properties and determine optimal excitation and emission figures. Fluoresence scans were conducted using a Hilachi F-4500 spectrofluorometer. The results of Table III illustrate that many types of foods contain measurable fluorescence which may be monitored for the purposes of this invention.

TABLE III

| Food Type | Fluorescence | EX(nm) | EM(nm) |
|---|---|---|---|
| Refined, bleached and dewaxed sunflower | 8116 | 370 | 465 |
| Refined, bleached sunflower | 7280 | 370 | 460 |
| Crude sunflower | 1541 | 385 | 510 |
| Water degummed Linseed oil | 5416 | 375 | 495 |
| Water degummed Linseed oil | 206 | 360 | 520 |
| Water degummed Canola | 189 | 360 | 520 |
| Beef Tallow | 1248 | 500 | 550 |

Changes can be made in the composition, operation and arrangement of the method of the present invention described herein without departing from the concept and scope of the invention as defined in the following claims:

We claim:

1. A method for the monitoring of the variation in amount of fluorescing impurities during food processing in food process streams which contain fluorescing impurities comprising the steps of:

A) adding a known amount of a substantially inert fluorescent material to said food process stream;

B) measuring the fluorescence emission wavelengths of the fluorescent impurity and the fluorescent material of step A over time utilizing a fluorometer;

C) calculating the ratio of the fluorescence of the fluorescent impurity to the fluorescence of the fluorescent material of step A;

D) determining from the change in the ratio of step C over time that a variation in the amount of the fluorescing impurity in the food process stream has occurred; and E) adjusting the food process appropriately to compensate for the measured variation in the amount of the fluorescing impurity in said food process stream.

2. The method of claim 1 wherein the fluorescent material is selected from the group consisting of naphthalene sulfonate salt, mono- and dimethyl naphthalene sulfonate salt, 1,5 naphthalene disulfonate salt, 2-naphthalene sulfonate salt, riboflavin, tyrosine, beta carotene, 1-tryptophan, sodium lignosulfonate, sodium humate, fluorescene and 1-dopa.

3. The method of claim 2 wherein the food process stream is selected from the group consisting of meat, vegetable oil, sugar beet, sugar cane, grain, poultry, fruit and soybean processing streams.

4. The method of claim 2 wherein the food process stream is a sugar beet processing stream and the fluorescent material is mono- and dimethyl naphthalene sulfonate salt.

5. The method of claim 2 wherein the food process is selected from the group consisting of boiling, chilling, drying, purifying, crystallizing, extracting, pasteurizing, thermal processing, grinding, pH adjustment, softening, waste treatment and clarifying.

6. The method of claim 2 wherein the concentration of the fluorescent material added to the food process stream is from about 0.1 ppb to about 250 ppm.

7. The method of claim 2 wherein the concentration of the fluorescent material added to the food process stream is from about 0.5 ppb to about 100 ppm.

8. The method of claim 2 wherein the concentration of the fluorescent material added to the food process stream is from about 1 ppb to about 25 ppm.

9. The method of claim 2 wherein the measurement of the fluorescence is continuously monitored by a fluorometer.

10. A method for the determination of the presence of contaminating food process streams which contain fluorescent moieties in the circulating water of food processing equipment which contains circulating water comprising the steps of:

A) adding a known amount of a substantially inert fluorescent material to said circulating waters;

B) measuring the fluorescence emission wavelengths of the fluorescent moiety and the fluorescent material of step A over time utilizing a fluorometer;

C) calculating the ratio of the fluorescence of the fluorescent moiety to the fluorescence of the fluorescent material of step A;

D) determining from the change in the ratio of step C over time that a contamination of the circulating water of the food processing equipment has occurred; and E) adjusting the food process appropriately to avoid further contamination of said food processing equipment.

11. The method of claim 10 wherein the fluorescent material is selected from the group consisting of naphthalene sulfonate salt, mono- and dimethyl naphthalene sulfonate salt, 1,5 naphthalene disulfonate salt, 2-naphthalene sulfonate salt, riboflavin, tyrosine, beta carotene, 1-tryptophan, sodium lignosulfonate, sodium humate, fluorescene and 1-dopa.

12. The method of claim 11 wherein the food process stream is selected from the group consisting of meat, vegetable oil, sugar beet, sugar cane, grain, poultry, fruit and soybean processing streams.

13. The method of claim 11 wherein the food process stream is a sugar beet processing stream and the fluorescent material is mono- and dimethyl naphthalene sulfonate salt.

14. The method of claim 11 wherein the food processing equipment which contains circulating water is selected from the group consisting of boilers, chillers, evaporators, pasteurizers, and thermal processors.

15. The method of claim 11 wherein the concentration of the fluorescent material added to the food process stream is from about 0.1 ppb to about 250 ppm.

16. The method of claim 11 wherein the concentration of the fluorescent material added to the food process stream is from about 0.5 ppb to about 100 ppm.

17. The method of claim 11 wherein the concentration of the fluorescent material added to the food process stream is from about 1 ppb to about 25 ppm.

18. The method of claim 11 wherein the measurement of the fluorescence is continuously monitored by a fluorometer.

19. A method for quantifying the amount of a food substance present in a food processing stream wherein the food substance is present in a known ratio to a fluorescing moiety in the food processing stream comprising the steps of:

A) adding a known amount of a substantially inert fluorescent material to said food process stream;

B) measuring the fluorescence emission wavelengths of the fluorescing moiety and the fluorescent material of step A over time utilizing a fluorometer;

C) calculating the ratio of the fluorescence of the fluorescent moiety to the fluorescence of the fluorescent material of step A; and D) determining from the change in the ratio of step C over time that a proportional variation in the amount of the food substance in said food processing stream has occurred.

20. The method of claim 19 wherein the fluorescent material is selected from the group consisting of naphthalene sulfonate salt, mono- and dimethyl naphthalene sulfonate salt, 1,5 naphthalene disulfonate salt, 2-naphthalene sulfonate salt, riboflavin, tyrosine, beta carotene, 1-tryptophan, sodium lignosulfonate, sodium humate, fluorescene and 1-dopa.

21. The method of claim 20 wherein the food processing stream is selected from the group consisting of meat, vegetable oil, sugar beet, sugar cane, grain, poultry, fruit and soybean processing streams.

22. The method of claim 20 wherein the food substance is selected from the group consisting of meat, poultry, beet sugar, sugar cane, grain, soybeans, fruit and vegetable oil.

23. The method of claim 20 wherein the food processing stream is a sugar beet processing stream and the fluorescent material is mono- and dimethyl naphthalene sulfonate salt.

24. The method of claim 20 wherein the fluorescing moiety is selected from the group consisting of: DC Red 22, DC Green 8, FDC Red 2, DC Yellow 10, DC Green 5, FDC Blue 1, FDC Blue 2, FDC Yellow 5 and FDC Yellow 6.

25. The method of claim 20 wherein the concentration of the fluorescent material added to the food process stream is from about 0.1 ppb to about 250 ppm.

26. The method of claim 20 wherein the concentration of the fluorescent material added to the food process stream is from about 0.5 ppb to about 100 ppm.

27. The method of claim 20 wherein the concentration of the fluorescent material added to the food process stream is from about 1 ppb to about 25 ppm.

28. The method of claim 20 wherein the measurement of the fluorescence is continuously monitored by a fluorometer.

29. The method of claim 20 wherein the food process is adjusted appropriately to compensate for the variation in the amount of the food substance in said food processing stream.

* * * * *